(12) United States Patent
Resh et al.

(10) Patent No.: US 6,890,954 B1
(45) Date of Patent: May 10, 2005

(54) USES OF 2-BROMOPALMITATE IN THE TREATMENT OF AUTOIMMUNE DISEASE

(76) Inventors: Marilyn D. Resh, 333 E. 79th St., Apt., 15X, New York, NY (US) 10021; Yael Webb, 58 Hapalmoch St., Haifa (IL)

( * ) Notice: Subject to any disclaimer, the term of this patent is extended or adjusted under 35 U.S.C. 154(b) by 249 days.

(21) Appl. No.: 10/089,141

(22) PCT Filed: Sep. 22, 2000

(86) PCT No.: PCT/US00/26190

§ 371 (c)(1),
(2), (4) Date: Aug. 14, 2002

(87) PCT Pub. No.: WO01/21173

PCT Pub. Date: Mar. 29, 2001

Related U.S. Application Data

(60) Provisional application No. 60/155,743, filed on Sep. 23, 1999.

(51) Int. Cl.⁷ .............................................. A61K 31/20
(52) U.S. Cl. ...................................................... 514/558
(58) Field of Search ......................................... 514/558

(56) References Cited

U.S. PATENT DOCUMENTS 5,714,516 A * 2/1998 Harper et al. ............... 514/558

* cited by examiner

Primary Examiner—Raymond J. Henley, III
Assistant Examiner—Leslie A. Royds
(74) Attorney, Agent, or Firm—Benjamin Aaron Adler

(57) ABSTRACT

The present invention provides a method of inhibiting Fyn/Lck fatty acylation and protein palmitoylation in a cell in an individual in need of such treatment comprising the step of administering to said individual a pharmacologically effective dose of 2-bromopalmitate. Also provided is a method of treating an individual having an autoimmune disease comprising the step of administering to said individual a pharmacologically effective dose of 2-bromopalmitate.

9 Claims, 16 Drawing Sheets

USES OF 2-BROMOPALMITATE IN THE TREATMENT OF AUTOIMMUNE DISEASE

CROSS REFERENCE TO RELATED APPLICATION

This is a 371 of PCT/US00/26190 filed Sep. 22, 2000 and claims benefit of priority of U.S. Provisional Application No. 60/155,743, filed Sep. 23, 1999, now abandoned.

FEDERAL FUNDING LEGEND

This invention was produced in part using funds obtained through grants GM57966 and CA29502 from the National Institute of Health. Consequently, the federal government has certain rights in this invention.

BACKGROUND OF THE INVENTION

1. Field of the Invention

The present invention relates generally to the fields of the molecular biology of T cell signaling and fatty acid biochemistry and pharmacology. More specifically, the present invention relates to novel uses of 2-bromopalmitate.

2. Description of the Related Art

Many viral and cellular proteins are modified by fatty acid acylation with myristate or palmitate (1,2). For example, all members of the Src family of tyrosine protein kinases are covalently modified by the 14 carbon fatty acid myristate. Myristate is co-translationally attached to a glycine at position 2 of the protein through an amide linkage, in a process catalyzed by N-myristoyl transferase (NMT) (35). Myristoylation has been shown to be necessary (6,7) but not sufficient (8) for membrane binding. In addition, all Src proteins use a second membrane targeting signal. For seven out of the nine Src family members, this second signal involves modification with the 16 carbon fatty acid palmitate. Palmitate is post-translationally attached to a cysteine residue within an N-terminal myr-gly-cys consensus motif (9).

Attachment of myristate and palmitate to Src family kinases enhances the localization of these proteins to the plasma membrane, where they must be present in order to function properly. In addition, protein palmitoylation has been shown to be critical for localization of proteins to specialized subdomains of the plasma membrane that are resistant to detergent extraction (10–15). These detergent resistant microdomains (detergent resistant microdomains), also known as rafts, are enriched in cholesterol, glycosphingolipids, and GPI-anchored proteins (16–18). Localization to detergent resistant microdomains influences the ability of key signaling molecules to interact with each other and to participate in signaling from the cell surface to the interior of the cell (11,19–21).

The importance of protein fatty acylation is best illustrated 0.5 in T cell receptor (TCR) mediated signal transduction. The Src related kinases Fyn and Lck are highly expressed in cells of hematopoietic origin, particularly lymphocytes (22), and are required for signaling through the T cell receptor. Protein tyrosine phosphorylation is one of the first events that occurs after binding of antigens to surface receptors in T lymphocytes. Upon receptor engagement, Fyn and Lck phosphorylate tyrosine residues found within multiple immunoreceptor tyrosine-based activation motifs (ITAMS) located on the cytosolic portions of the TCRζ and CD3 chains. Immunoreceptor tyrosine-based activation motifs phosphorylation recruits key molecules that mediate downstream signaling, including the tyrosine kinase ZAP-70 (19). One of the targets for activated ZAP-70 is LAT, a palmitoylated transmembrane protein (10). Several recent studies have established that the ability of Lck, Fyn and LAT to function in T cell receptor-mediated signaling depends on their fatty acylation and localization to detergent resistant microdomains. Palmitoylation of Lck was shown to be essential for its signaling function in T lymphocytes (11). Fyn must be palmitoylated and localized to detergent resistant microdomains in order to interact with the ζ chain of the T cell receptor (23). Moreover, LAT must be palmitoylated and in detergent resistant microdomains in order to become tyrosine phosphorylated and participate in downstream signaling (20).

To date, studies of the role of protein palmitoylation in various cellular pathways have suffered from two major drawbacks. First, in contrast to N-myristoylation, very little is known about the enzymology and biochemistry of protein palmitoylation. Two thioesterases, PPT1 and AP1, have been identified that deacylate palmitoylated Ras and Gα proteins in vitro (24,25). However, the enzyme(s) that catalyze(s) attachment of palmitate to proteins have not been definitively identified. Several recent studies have described purification of palmitoyl acyl transferase (PAT) activities (26–28), while other reports have documented that non-enzymatic palmitoylation can occur under certain conditions in vitro (29,30). Second, nearly all studies reported to date on the role of palmitoylation in cellular functions have been limited to expressing non-acylated mutant forms of proteins in various systems (11,20). While this approach does provide useful information, it is limited by the need to overexpress the mutant proteins. Furthermore, the loss of a cysteine residue, and not the loss of palmitate per se, may impair the ability of the protein to function properly. For example, Hepler et al showed that cysteine residues at the amino terminus of the Gq alpha subunit is important for its interaction with effector and receptor molecules, regardless of their state of palmitoylation (31).

Polyunsaturated fatty acids (PUFAs), particularly the n-3 series, are used clinically as immunosuppressive agents (32) and in the treatment of various inflammatory diseases (33–36). Recently, it was reported that polyunsaturated fatty acids inhibit T cell signal transduction by displacing Fyn and Lck from the detergent resistant microdomains (37). The inhibitory effects of polyunsaturated fatty acids were hypothesized to be mediated by modification of DRM structure and composition.

The prior art is deficient in the lack of specific inhibitors of Fyn and Lck fatty acylation and protein palmitoylation. The present invention fulfills this longstanding need and desire in the art.

SUMMARY OF THE INVENTION

The present invention documents the discovery of 2-bromopalmitate as an inhibitor of Fyn/Lck fatty acylation in general, and palmitoylation in particular. 2-bromopalmitate preferentially blocks palmitoylation of N-terminally palmitoylated proteins, and inhibits membrane binding and localization of Fyn to detergent resistant microdomains in COS-1 cells. Moreover, treatment of Jurkat T cells with 2-bromopalmitate partially blocks localization of endogenous Fyn, Lck and LAT to rafts, and inhibits T cell receptor-mediated signaling events including enhanced tyrosine phosphorylation, calcium flux and activation of MAP kinase. The identification of 2-bromopalmitate as an inhibitor of fatty acylation of Src family kinases serves to provide insight into the role of protein palmitoylation in Src mediated signal tranduction pathways.

The present invention also demonstrates that polyunsaturated fatty acids are inhibitors of Fyn palmitoylation, and discloses a novel mechanism of action by which these agents exert their immunosuppressive effects.

In one embodiment of the present invention, there is provided a method of inhibiting Fyn/Lck fatty acylation and protein palmitoylation in a cell in an individual in need of such treatment comprising the step of administering to said individual a pharmacologically effective dose of 2-bromopalmitate.

In another embodiment of the present invention, there is provided a method of treating an individual having a pathophysiological state comprising the step of administering to said individual a pharmacologically effective dose of 2-bromopalmitate.

In yet another embodiment of the present invention, there is provided a pharmaceutical composition comprising 2-bromopalmitate and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the effect of 2-bromopalmitate on Fyn fatty acylation and subcellular localization in COS-1 cells. Transfected cells were preincubated overnight with 100 μM 2-bromopalmitate, as described below.

FIG. 2 shows the effect of 2-bromopalmitate on localization of Fyn(16)-eGFP in COS-1 cells.

FIG. 3 shows the effect of 2-bromopalmitate on subcellular localization of palmitoylated proteins. COS-1 cells were transiently transfected and treated as follows.

FIG. 4 shows the effect of 2-bromopalmitate on Fyn fatty acylation and DRM localization of palmitoylated proteins in Jurkat T cells. Cells were transfected by electroporation a nd preincubated for 3 hours with 100 μM 2-bromopalmitate, as described below.

FIG. 5 shows tyrosine phosphorylation of signaling proteins in Jurkat T cells.

FIGS. 6A-1 and 2 shows calcium mobilization in Jurkat T cells. FIG. 6A: untreated cells were preincubated with Fluo 3 as indicated below and calcium release was measured by flow cytometry. Top: After obtaining a background fluorescence (Baseline), cells were activated with OKT3 mAb, and fluorescence was measured for the indicated time (post OKT3). Bottom: Quantations of fluorescence before (left—baseline) and after (right—post OKT3) CD3 stimulation.

FIGS. 6B-1 and 2 cells were pretreated with 2-bromopalmitate and analyzed as described in FIGS. A-1 and 2).

FIG. 8 shows the effect of polyunsaturated fatty acids on Fyn fatty acylation and localization to detergent resistant microdomains in COS-1 cells. Cells expressing Fyn were preincubated overnight with 50 µM arachidonic acid (20:4) or eicosapentaenoic acid (20:5) or left untreated (C), as described below.

DETAILED DESCRIPTION OF THE INVENTION

Figure 1A:
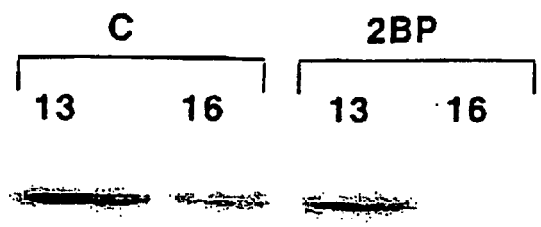
FIG. 1A: cells were radiolabeled for 4 hours in the absence (C) or presence (2BP) of 2-bromopalmitate with 125I-IC13 or 125I-IC16 (top panel), or with Tran35S-label (bottom panel), lysed and subjected to immunoprecipitation with anti-Fyn antibody. Lysates were subjected to SDS-PAGE followed by phosphorimaging.
Figure 1A:
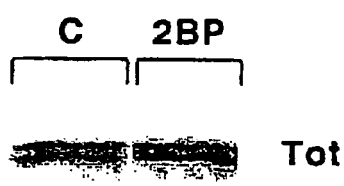

This invention describes a palmitate analog, 2bromopalmitate, that effectively blocks Fyn fatty acylation in general, and palmitoylation in particular. Treatment of COS-1 cells with 2-bromopalmitate blocked myristoylation and palmitoylation of Fyn, and inhibited membrane binding and localization of Fyn to detergent resistant membranes (DRMs)[1]. In Jurkat T cells, 2-bromopalmitate blocked localization of the endogenous palmitoylated proteins Fyn, Lck and LAT to detergent resistant microdomains. This resulted in impaired signaling through the T cell receptor as evidenced by reductions in tyrosine phosphorylation, calcium release and activation of MAP kinase. The polyunsaturated fatty acids arachidonic acid and eicosapentaenoic acid inhibit Fyn palmitoylation and consequently block Fyn localization to detergent resistant microdomains.

[1]Abbreviations: DRMs, detergent resistant microdomains, ITAM, immunereceptor tyrosine-based activation motif; PUFAs, polyunsaturated fatty acids; GFP, Green Fluorescent Protein; IC13, 13-iodotridecanoic acid; IC16, 16-iodohexadecanoic acid; NMT, N-myristoyl transferase; PAT, palmitoyl acyl transferase; TCR, T cell receptor.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes": [IRL Press, (1986)]; B. Perbal, "A Practical Guide To Molecular Cloning" (1984).

The present invention is directed to a method of inhibiting Fyn/Lck fatty acylation and protein palmitoylation in a cell in an individual in need of such treatment comprising the step of administering to said individual a pharmacologically effective dose of 2-bromopalmitate. Preferably, the 2-bromopalmitate is administered in a dose of from about 0.1 mg/kg to about 100 mg/kg of total body weight of said individual. Administration of 2-bromopalmitate inhibits N-terminally palmitoylated proteins, myristoylation of proteins and T cell signalling events. In one aspect, the individual has a autoimmune disease. Representative examples of autoimmune disease include rheumatoid arthritis, Crohn's disease, diabetes, multiple sclerosis and systemic lupus erythematosus.

The present invention is directed to a method of treating an individual having a pathophysiological state comprising the step of administering to said individual a pharmacologically effective dose of 2-bromopalmitate. Preferably, the individual has an autoimmune disease or abnormal T cell signalling.

The present invention is also directed to a pharmaceutical compositions containing 2-bromopalmitate. In such a case, the pharmaceutical composition comprises 2-bromopalmitate and a pharmaceutically acceptable carrier. A person having ordinary skill in this art would readily be able to determine, without undue experimentation, the appropriate dosages and routes of administration of 2-bromopalmitate.

Compounds of the present invention, pharmaceutically acceptable salt thereof and pharmaceutical compositions incorporating such, may be conveniently administered by any of the routes conventionally used for drug administration, e.g., orally, topically, parenterally, or by inhalation. 2-bromopalmitate may be administered in conventional dosage forms prepared by combining the compound with standard pharmaceutical carriers according to conventional procedures. 2-bromopalmitate may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well known variable. The carrier(s) must be "acceptable" in the sense of being compatible with the other ingredients of the formulation and not deleterious to the recipient thereof.

The pharaceutical carrier employed may be, for example, either a solid or a liquid. Representative solid carriers are lactose, terra alba, sucrose, talc, gelatin, agar, pectin, acacia, magnesium sterate, stearic acid and the like. Representative liquid carriers include syrup, peanut oil, olive oil, water and the like. Similarly, the carrier may include time delay material well known in the art such as glyceryl monosterate or glyceryl disterarate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension.

2-bromopalmitate may be administered topically (nonsystemically). This includes the application of 2-bromopalmitate externally to the epidermis or the buccal cavity and the instillation of such a compound into the ear, eye and nose, such that the compound does not significantly enter the bloodstream. Formulation suitable for topical administration include liquid or semi-liquid preparations suitable for penetration through the skin to the site of inflammation such as liniments, lotions, creams, ointments, pastes and drops suitable for administration to the ear, eye and nose. The active ingredient may comprise, for topical administration from 0.001% to 10% w/w, for instance from 1% to 2% by weight of the Formulation. It may however, comprise as much as 10% w/w but preferably will comprise less than 5% w/w, more preferably from 0.1% to 1% w/w of the Formulation.

Lotions according to the present invention include those suitable for application to the skin and eye. An eye lotion may comprise a sterile aqueous solution optionally containing a bactericide and may be prepared by methods similar to those for the preparation of drops. Lotions or liniments for application to the skin may include an agent to hasten drying and to cool the skin, such as an alcohol or acetone, and/or a moisterizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap, a mucilage, an oil of natural origin such as almond, corn, archis, castor, or olive oil; wool fat or its derivatives or a fatty acid such as steric or oleic acid together with an alcohol such as propylene glycol or a macrogel. The formulation may incorporate any suitable surface active agent such as an anionic, cationic or non-ionic ionic surfactant such as a sorbitan ester or a polyoxyethylene derivative thereof. Suspending agents such as natural gums, cellulose derivatives or inorganic materials such as silicaceous silicas, and other ingredients such as lanolin may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving. Alternatively, the solution may be sterilized by filtration and transferred to the container by an aseptic technique. Examples of bactericidal and fungicidal agents suitable for inclusion in the drops are phenymercuric nitrate or acetate (~0.002%), benzalkonium chloride (~0.01%) and chlorhexidine acetate (~0.01%). Suitable solvents for the preparation of an oily solution include glycerol, diluted alcohol and propylene glycol.

2-bromopalmitate may be administered parenterally, i.e., by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. Compounds may also be administered by inhalation, e.g., intranasal and oral inhalation administration. Appropriate dosage forms for such administration, such as aerosol formulation or a metered dose inhaler may be prepared by conventional techniques well known to those having ordinary skill in this art.

For all methods of use disclosed herein for 2-bromopalmitate, the daily oral dosage regiment will preferably be from about 0.1 to about 100 mg/kg of total body weight. The daily parenteral dosage regimen will preferably be from about 0.1 to about 100 mg/kg of total body weight. The daily topical dosage regimen will preferably be from about 0.01 to about 1 g, administered one to four, preferably two to three times daily. It will also be recognized by one of skill in this art that the optimal quantity and spacing of individual dosages of 2-bromopalmitate, or a pharmaceutically acceptable salt thereof, will be determined by the nature and extent of the condition being treated and that such optimums can be determined by conventional techniques.

Suitable pharmaceutically acceptable salts are well known to those skilled in the art and include basic salts of inorganic and organic acids, such as hydrochloric acid, hydrobromic acid, sulphuric acid, phophoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of 2-bromopalmitate may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

Autoimmune diseases are characterized by immune cell destruction of self cells, tissues and organs. Representative examples of such autoimmune diaseases are rheumatoid arthritis diabetes, multiple sclerosis, Crohn's disease and systemic lupus erythematosus. 2-bromopalmitate has potential uses in other immune cell functions. For example, the IgE receptor uses palmitoylated Lyn (another Src kinase family member) to signal for the inflammatory response and Lyn must be palmitoylated and in membrane rafts in order to function. Thus, 2-bromopalmitate could be used as an anti-inflammatory agent.

The following examples are given for the purpose of illustrating various embodiments of the invention and are not meant to limit the present invention in any fashion.

EXAMPLE 1

Cell Culture and Transfections

COS-1 cells were maintained and transfected as previously described (9). Transfection with FUGENE™ 6 Transfection Reagent (Boehringer Mannheim) was carried out according to the manufacturer's instructions. Jurkat T cells were maintained in RPMI 1640 supplemented with 10% FBS, 100 μg of penicillin and streptomycin per ml and 100 μg of sodium pyruvate and glutamine per ml. Cells were transfected by electroporation as previously described (38).

EXAMPLE 2

Antibodies

Monoclonal anti-Fyn and anti-Lck antibodies used for Western blotting were purchased from Transduction Laboratories (Lexington, Ky.). The rabbit polyclonal antiserum to Fyn used for immunoprecipitation was described previously (13). Monoclonal anti-PLCγ-1 and rabbit polyclonals anti-LAT, anti PI3 kinase, anti-Vav and anti-ZAP-70 were purchased from Upstate Biotechnology (Lake Placid, N.Y.). Monoclonals anti-Hras, anti-p-ERK anti-P-Tyr (PY99) and agarose-conjugated PY99 were purchased from Santa Cruz Biotechnology (Santa Cruz, Calif.). Anti MAPK antibody was purchased from New England Biolabs (Beverly, Mass.). Fluorescein (FITC)-conjugated Goat Anti-Mouse secondary antibody was purchased from Jackson ImmunoResearch Laboratories (West Grove, Pa.). Anti GFP antibody was purchased from CLONTECH Laboratories (Palo Alto, Calif.).

EXAMPLE 3

Fyn Chimeras

The Fyn Chimeras $G\alpha_o(10)$Fyn and GAP43(10)-Fyn have been described previously (12). G2A, C35 Fyn-HRas was constructed as follows. An antisense oligonucleotide primer was designed that corresponded to the last 6 amino acids of Fyn fused in frame to the C-terminal 12 amino acids of H-Ras, followed by a stop codon, a SalI site and a GIC clamp. A sense primer that began 57 bases upstream of a unique BglII site in Fyn was constructed. These two primers were used in a PCR reaction to amplify a fragment containing the C-terminal region of Fyn fused to the H-Ras tail. The PCR reaction product was cut with BglII and SalI and used to replace the corresponding region of Fyn in G2AFyn/pSP65. G2A Fyn HRas/pSP65 was then digested with NcoI and BglII to remove the 5' coding region of Fyn, and ligated to a 1.7 kb NcoI/BglII fragment from another Fyn clone containing the G2A, C3S mutation. G2A, C3S Fyn-HRas/pSP65 was digested with EcoRI and SalI and ligated into EcoRI and SalI cut pCMV5. The construct was verified by DNA sequencing prior to use in transfections.

EXAMPLE 4
Cell Labeling

The syntheses of 13-$[^{125}I]$-iodotridecanoic acid (IC13) or 16-$[^{125}I]$-iodohexanoic acid (IC16) were carried out as described previously (39). Cell labeling was carried out as described (12,13) with modifications. Briefly, each 60 mm plate of Fyn transfected COS-1 cells was incubated O/N in DMEM containing 2.5% FBS, 0.5% defatted BSA (Sigma) with or without 100 µM 2-bromopalmitate or 50 µM polyunsaturated fatty acid. Prior to labeling, the cells were incubated for 1 hr with 1 ml of DMEM containing 2% dialyzed FBS, then labeled for 4 hours with 25–50 µCi IC13 or IC16 in DMEM containing 2% dialyzed FBS, 0.5% defatted BSA with or without 2-bromopalmitate or polyunsaturated fatty acid. Labeled cells were washed three times with cold STE (100 mM NaCl, 10 mM Tris pH 7.4, 1 mM EDTA) and lysed in 0.6 ml of cold RIPA buffer containing protease inhibitors (10 µg/ml each of benzamidine, AEBSF, TPCK and TLCK, 1.5 µg/ml each of Leupeptin, Pepstatin A and Aprotinin). Lysates were clarified at 100,000×g for 15 min at 4° C. in a Beckman TL-100 ultracentrifuge. Lysates were immunoprecipitated with rabbit anti-Fyn antibody and protein A-agarose. Immunoprecipitates were washed three times with cold RIPA buffer and suspended in 1× sample buffer containing 100 mM dithiothreitol and subjected to SDS-PAGE. Gels were dried between cellophane and analyzed by phosphorimaging after 12–36 hours exposure. Experiments in Jurkat T cells were carried out according to the above protocol using 2×10$^7$ cells per experiment, and reducing the incubation time with 2-bromopalmitate to 3–4 hours.

EXAMPLE 5
Subcellular Cell Fractionation

Each 60 mm plate of Fyn transfected COS-1 cells was starved for 1 hour in DMEM containing 2.5% FBS and 0.5% defatted BSA with or without 100 µM 2-bromopalmitate. After overnight culture at 37° C., the cells were fractionated into P100 and S100 fractions, immunoprecipitated with anti-Fyn antibody, subjected to SDS-PAGE, and immunoblotted with anti-Fyn antibody as previously described (9,12, 13).

Analysis of the G2A,C3S Fyn-HRas chimera was performed according to the procedure described above. Analysis of the G12V HRas construct was according to the procedure described above, except that the samples were not immunoprecipitated, and were subjected to immunoblotting with anti-HRas antibody.

For analysis of newly synthesized Fyn, cells were cultured overnight as descibed above, then starved for 1 hr in DMEM minus methionine and cysteine containing 2% dialyzed FBS, 0.5% defatted BSA with or without 100 µM 2-bromopalmitate. Cells were labeled for 5 minutes with Trans$^{35}$S-Label (ICN, Irvine, Calif.), then fractionated as described above. Gels were treated for 20 minutes with 1M salicylic acid prior to drying. The Gαo(10)-Fyn chimera was labeled for 5 min and GAP-43 Fyn chimera was labeled for 2 hours and fractionated according to the above conditions.

EXAMPLE 6
Immunofluorescence Microscopy

COS-1 cells were transfected with a Fyn(16)-eGFP construct (12) and seeded onto 25-mm glass coverslips 2 days prior to the experiment. Cells were treated overnight with or without 2 bromopalmitate as described above. Plates were washed with PBS and coverslips were mounted onto glass slides in PBS and observed with a 40× and 100×oil immersion lens on a Zeiss Axiophot 2 microscope and photographed with Kodak TMAX 400.

EXAMPLE 7
T cell Activation and Phosphotyrosine Immunoblots

Jurkat T cells (2×10$^6$–1×10$^7$) were centrifuged at 1,000×g for 5 minutes, rinsed with RPMI, resuspended in RPMI supplemented with 2% dialyzed FBS, 0.5% defatted BSA, and incubated with or without 100 µM 2-bromopalmitate at 8×10$^5$ cells/ml for 3 hours. The cells were centrifuged, washed with RPMI and resuspended in RPMI at 1×10$^7$–1× 10$^8$ cells/ml. The cells were then activated with anti-CD3 OKT3 mAb (0.3 mg/ml) for 3 min at 37° C., quickly spun down, washed once with cold RPMI and once with cold STE, and lysed in RIPA Samples were solubilized in 1× sample buffer containing 5% β-mercaptoethanol and subjected to SDS-PAGE, followed by immunoblotting with anti-phosphotyrosine antibody (PY99). For analysis of specific proteins, RIPA lysates were immunoprecipitated with the specific antibodies O/N, and immunoblotted for phosphotyrosine. Alternatively, proteins were immunoprecipitated with agarose-conjugated anti phosphotyrosine antibody and blotted for the specific proteins.

EXAMPLE 8
Isolation of DRMs

Isolation of Triton X-100 resistant and soluble fractions was carried out as described previously (12). Isolation of detergent resistant microdomains by sucrose gradients were carried out as follows (19): Jurkat cells (5×10$^7$) were treated with 2-bromopalmitate, activated with OKT3 mAb as described above, and lysed in 1 ml lysis buffer (25 mM MES pH 6.5, 150 mM NaCl, 0.5% Triton X-100, 1 mM Na$_3$VO$_4$) supplemented with protease inhibitors for 30 minutes at 0° C. After homogenizing 10 times with a loose fit Dounce homogenizer, lysates were mixed with 1 ml 85% sucrose in MBS (25 mM MES pH 6.5, 150 mM NaCl), and overlayered with 6 ml 30% sucrose in MBS, then with 4 ml 5% sucrose in MBS. Following centrifugation for 16 hours at 145,000 g in an SW40 rotor, 1 ml fractions were collected and analyzed by PAGE and immunoblotting with anti-Fyn, anti-LAT, or anti-Lck antibodies.

For isolation of detergent resistant microdomains in PUFA-treated COS-1 cells, a confluent 100 mm plate of COS-1 cells transiently transfected with Fyn cDNA was washed with S-IE and subjected to the same procedure described above. Fractions were analyzed for the presence of Fyn by immunoblotting.

EXAMPLE 9
Calcium Mobilization Assay

Jurkat cells were treated with 2-bromopalmitate as described above. The cells (2×10$^5$) were collected by centrifugation and resuspended at 2×10$^6$ cells/ml in RPMI containing in 50 μM fluo-3 with or without 100 μM 2-bromopalmitate for 30 minutes at room temperature. Cells loaded with fluo-3 were then collected by centrigation, washed with Hank's Buffered Saline Solution (5.4 mM KCl, 0.3 mM Na$_2$HPO$_4$, 0.4 mM KH$_2$PO$_4$, 4 mM NaHCO$_3$, 1.3 mM CaCl$_2$, 0.5 mM MgCl$_2$, 0.6 mM MgSO$_4$, 137 mM NaCl, 5.6 mM glucose, 20 mM Hepes pH 7.4) and resuspended in the same buffer at 5×10$^5$ cells/ml at 37° C. To initiate calcium flux, the cells were activated with OKT3 antibody as described above, and analyzed for free calcium ion by measurement of fluo-3 fluoresence emission by flow cytometry.

For analysis of CD3 positive cells, 1×10$^6$ cells were centrifuged, washed and resuspended in 100 μl ice cold phosphate buffered saline (PBS-136 mM NaCl, 2.6 mM KCl, 4.3 mM Na$_2$HPO$_4$, 1.5 mM KH$_2$PO$_4$) containing 1% FBS. OKT3 antibody was added to a final concentration of 0.3 mg/ml. Following 30 minutes on ice, the cells were washed twice with PBS/1% FBS and incubated at 0° C. for an additional 30 minutes with an FITC-conjugated Goat Anti-Mouse secondary antibody (1:20 dilution). The cells were washed twice, resuspended in PBS/1% FBS, and subjected to FACS analysis.

EXAMPLE 10
Activation of MAP Kinase

Jurkat cells were treated with 2-bromopalmitate and activated as described above. Lysates were analyzed for the presence of active MAP kinase by immunoblotting with a pERK antibody, and for total MAP kinase by immunoblotting with an anti MAPK antibody.

EXAMPLE 11
Identification of 2-Bromopalmitate as an Inhibitor of Fyn Fatty Acylation A number of palmitic acid analogs were screened for their ability to inhibit Fyn palmitoylation. COS-1 cells were transfected with cDNA encoding Fyn. Three days after transfection, the cells were labeled with either [$^{35}$S]-methionine, 13-[$^{125}$I]-iodotridecanoic acid (IC13), an iodinated myristate analog, or 16-[$^{125}$I]-iodohexanoic acid (IC16), an iodinated palmitic acid analog (39), in the presence or absence of nonradioactive palmitate analogs. Cells were lysed, immunoprecipitated with anti-Fyn antibody, and analyzed by SDS-PAGE and phosphorimaging. 2-Bromopalmitate efficiently inhibited Fyn fatty acylation (FIG. 1A). When normalized for total protein levels, 70% of Fyn myristoylation and over 90% of Fyn palmitoylation was inhibited in the presence of 2-bromopalmitate. Treatment of cells with other analogs, including 2-hydroxypalmitate, palmitoleic acid and 16-hydroxypalmitate had no effect (data not shown).

EXAMPLE 12
Effect of 2-bromo-palmitate on Subcellular Localization of Fyn Newly synthesized Fyn becomes plasma membrane bound within 5 minutes after biosynthesis (12). The rapid membrane targeting is dependent on dual fatty acylation of Fyn with myristate and palmitate. The effect of 2-bromopalmitate on the ability of newly synthesized Fyn to localize to membranes was next examined. Transfected COS-1 cells were incubated for 12–16 hours with or without 100 μM 2-bromopalmitate. Cells were then metabolically labeled with [$^{35}$S]-methionine for 5 minutes followed by fractionation into cytosolic (S100) or membrane (P100) fractions.

Figure 1B:
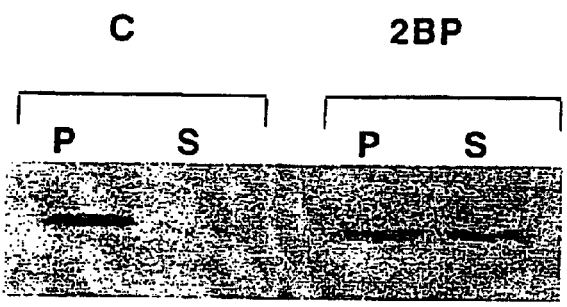
FIG. 1B: cells were radiolabeled with Tran$^{35}$S-label for 5 minutes, fractionated into particulate P100 (P) fractions and soluble S100 (S) fractions by centrifugation at 100,000×g, and subjected to immunoprecipitation, SDS-PAGE and phosphorimaging.

As depicted in FIG. 1B, in untreated cells, 90% of the labeled Fyn was membrane bound. In cells treated with 2-bromopalmitate, 50% of Fyn remained cytosolic, demonstrating the ability of the reagent to partially block membrane association of newly synthesized Fyn. The effect of 2-bromo-palmitate on membrane localization of steady-state Fyn was also examined. Transfected cells were treated with 2-bromo-palmitate as described above, then fractionated, immunoprecipitated with anti-Fyn followed by Western blotting with anti-Fyn antibody. The effect of 2-bromo-palmitate on membrane localization of steady-state Fyn was identical to the effect on newly synthesized Fyn, with 50% of the Fyn protein fractionating in the cytosol (data not shown). These results mimic the fractionation pattern of a non-palmitoylated Fyn mutant (C3,6SFyn), and of a non-myristoylated Fyn mutant (G2AFyn), and strongly suggest that the redistribution of Fyn observed in 2-bromopalmitate treated cells is due to inhibition of Fyn fatty acylation (13).

Previous experiments have shown that following rapid membrane binding of newly synthesized Fyn, there is a slower partitioning of Fyn (10–20 minutes) to regions of the plasma membrane that are resistant to Triton X-100 extraction at 4° C. (12). Therefore the effect of 2-bromopalmitate on the localization of Fyn to Triton X-100 insoluble fractions was examined. Transfected COS-1 cells were left untreated or treated with 2-bromopalmitate as described above. Cells were extracted with buffer containing 1% Triton X-100, and samples were subjected to immunoprecipitation and Western blotting with anti-Fyn antibodies.

Figure 1C:
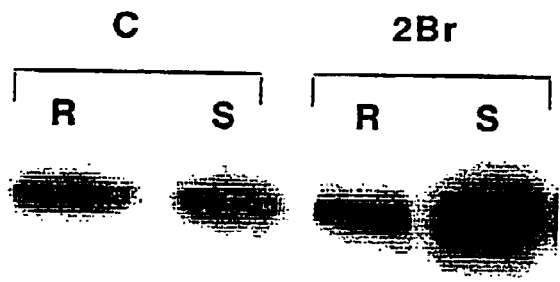
FIG. 1C: cells were lysed in buffer containing 1% Triton X-100. Detergent soluble (S) and resistant (R) fractions were clarified at 100,000×g and subjected to immunoprecipitation and SDS-PAGE followed by immunoblotting with anti Fyn antibodies.

As depicted in FIG. 1C, in untreated cells the majority of Fyn was associated with detergent resistant fractions (R), in agreement with previous experiments (12). In comparison, Fyn in 2-bromopalmitate treated cells was mostly soluble, demonstrating the ability of 2-bromopalmitate to partially block association of Fyn with detergent resistant membrane subdomains.

To investigate the effect of 2-bromopalmitate on the intracellular localization of Fyn more precisely, COS-1 cells expressing a Fyn(16)-eGFP construct were examined by immunofluorescence. This construct contains the first 16 amino acids of Fyn fused in frame to eGFP; the chimera is targeted to the plasma membrane and detergent resistant microdomains (12). Cells were cultured with no treatment, with 2-bromopalmitate or with 2-hydroxymyristate, a known myristoylation inhibitor (40,41), as described above, and were examined live by fluorescence microscopy.

Figure 2A:
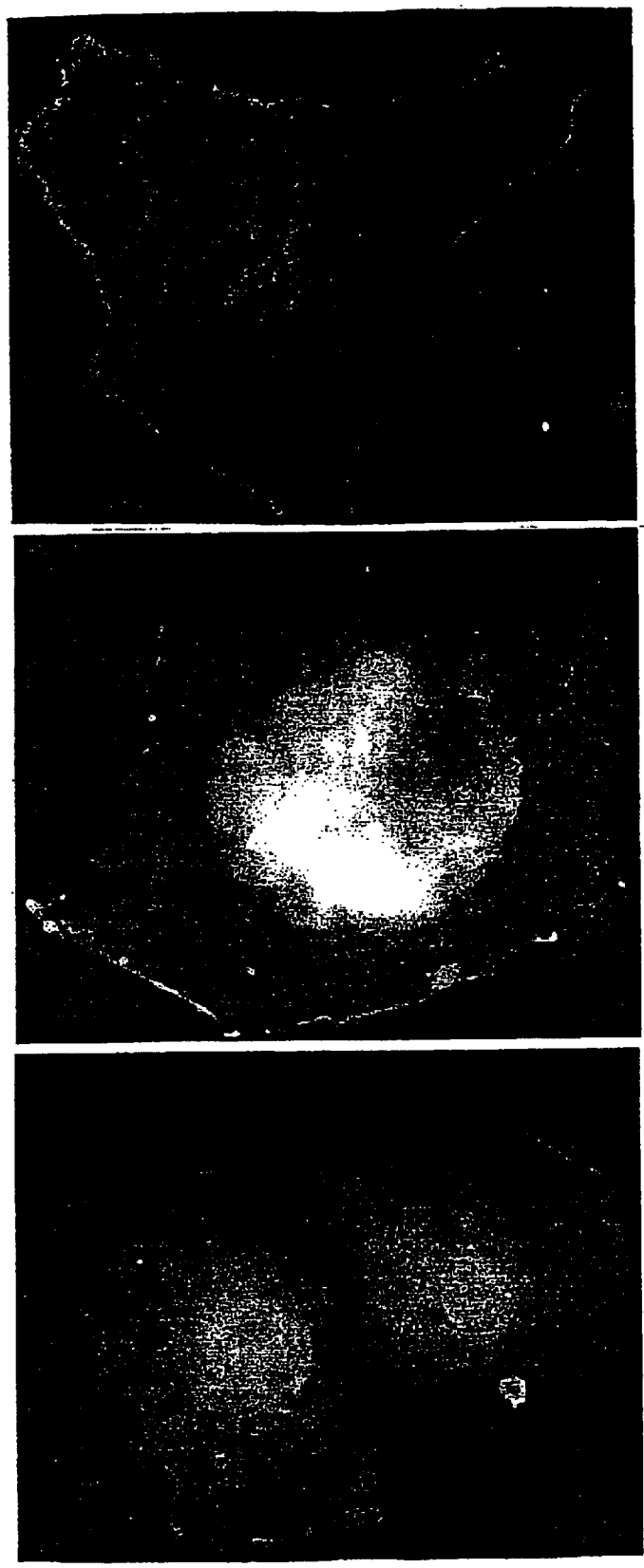
FIG. 2A: cells transiently expressing Fyn(16)-eGFP were preincubated overnight in the absence (top) or presence of 100 μM 2-bromopalmitate (middle) or 100 μM 2-hydroxymyristate (bottom) and examined live by fluorescence microscopy.
Figure 2B:
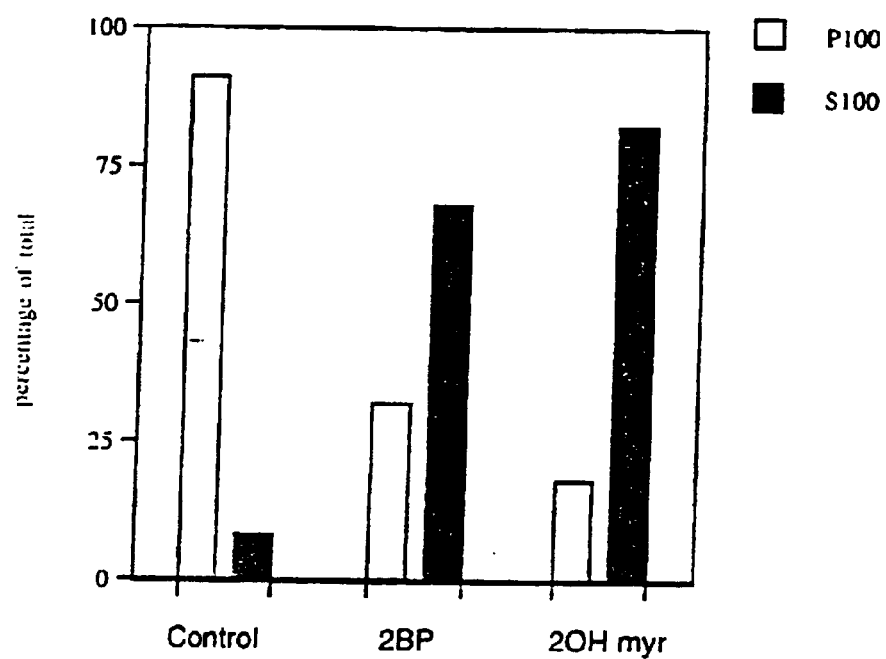
FIG. 2B: duplicates of the above samples were subjected to subcellular fractionation into P100 and S100 fractions and subjected to immunoblotting with anti-GFP antibody. 2BP: 2-bromopalmitate. 2OH myr: 2 hydroxymyristate.

FIG. 2A shows that Fyn(16)-eGFP is primarily distributed in the plasma membrane (Top). In contrast, cells treated with 2-bromopalmitate (middle) and 2-hydroxymyristate (bottom) showed reduced plasma membrane staining, and instead exhibited a distinct perinuclear staining, presumably representing cytosolic and intracellular membrane distribution. Analysis of the subcellular localization of Fyn(16)-eGFP in the presence of 2-bromopalmitate and 2-hydroxymyristate was performed as described above for steady-state Fyn. As depicted in FIG. 2B, in the absence of treatment, 80% of Fyn(16)-eGFP Fyn was membrane bound, whereas in cells treated with 2-bromopalmitate and 2-hydroxymyristate, 65% and 78% of Fyn(16)-eGFP were cytosolic, respectively. These results strengthen the hypothesis that fatty acylation of Fyn is important for the proper localization of the protein within the cell.

EXAMPLE 13
Effect of 2-bromo-palmitate on Membrane Localization of Other Palmitoylated Proteins Palmitoylation has been shown to occur on a wide variety of cellular proteins and the sites of palmitoylation can be quite diverse. Whether 2-bromopalmitate can inhibit palmitoylation and membrane binding of other palmitoylated proteins was next examined. Three representative palmitoylated protein sequences were chosen as model systems. The Gαo subunit of the heterotrimeric Go protein is myristoylated and palmitoylated on an N-terminal Gly-Cys motif, similar to Fyn and Lck (42,43). The neuronal protein GAP43 (neuromodulin) is palmitoylated near the N-terminus at cysteines 3 and 4, but is not myristoylated (44). Finally, the oncogenic H-Ras protein is palmitoylated just upstream of the C-terminal CAAX box (45).

Each of these three sequences was appended onto the Fyn protein. Gαo(10)-Fyn and GAP43(10)-Fyn are chimeric constructs with the first 10 amino acids of Gαo or GAP-43, respectively, in place of the first 10 amino acids of wt Fyn. These constructs have been previously described (12,13). In addition, the H-Ras tail was fused to the C-terminus of a non-acylated Fyn mutant (G2A,C3SFyn-HRas). This construct contains full length Fyn with mutations in the N-terminal myristoylation and palmitoylation sites, but with the C-terminus of H-Ras available for prenylation and palmitoylation.

Figure 3A:
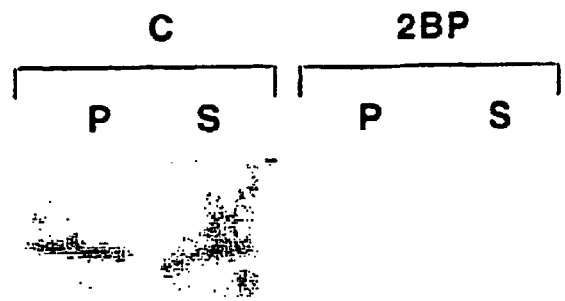
FIG. 3A: GαO(10)Fyn. Cells were treated overnight without (C) or with (2BP) 2-bromopalmitate, labeled for 5 minutes with Tran35S-label and subjected to cellular fractionation into P100 (P) and S100 (S) fractions, followed by immunoprecipitation with anti-Fyn antibody, SDS-PAGE and phosphorimaging.
Figure 3B:
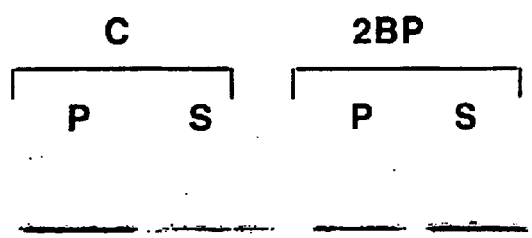
FIG. 3B: GAP43(10)-Fyn. Cells were treated with or without 2-bromopalmitate as in (FIG. 3A) with the exception of labeling for 2 hours, to allow newly synthesized protein to reach the plasma membrane.
Figure 3C:
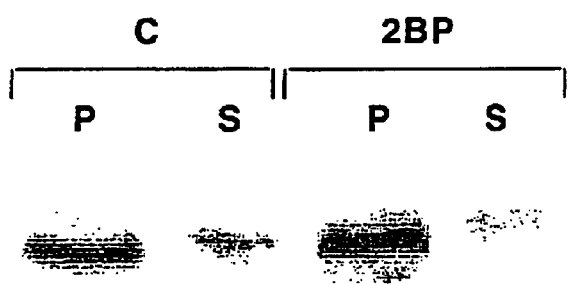
FIG. 3C: G2A, C3SFyn-HRas. Cells were treated with 2-bromopalmitate as in (FIG. 3A). After fractionation, lysates were subjected to immunoprecipitation followed by immunoblotting with anti-Fyn antibodies.
Figure 3D:
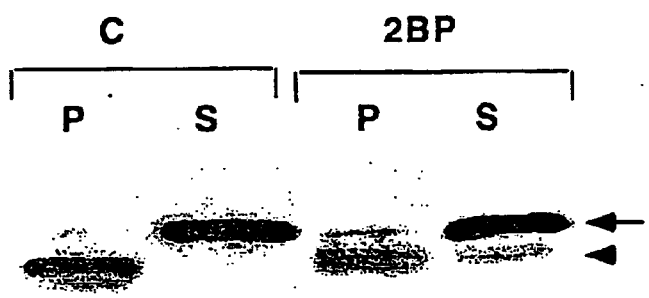
FIG. 3D: G12V-Hras. Cells were treated with or without 2-bromopalmitate as in (FIG. 3A) and fractionated, following by immunoblotting with anti Ras antibody. The faster migrating band represents processed Ras. The slower migrating band (( ) represents unprocessed, cytosolic Ras).

Finally, an oncogenic G12V full length H-Ras construct was tested. As depicted in FIGS. 3A and B, 2-bromopalmitate inhibited membrane binding of the two N-terminal palmitoylated proteins, GαO(10)-Fyn and GAP43(10)-Fyn, to the same extent as wt Fyn. In contrast, 2-bromopalmitate had only a minimal effect on the membrane localization of the two Ras constructs, inducing a 10–20% shift from membrane to cytosol (FIGS. 3C and D). The G12V H-Ras construct migrates as a doublet on a gel. The slower migrating form represents the non-processed cytosolic form of H-Ras, and the faster migrating form represents the processed Ras, which is membrane bound. Thus 2-bromopalmitate appears to possess some specificity towards inhibiting membrane localization of N-terminal palmitoylated proteins, in comparison to a protein palmitoylated near the C-terminus. The absolute sequence surrounding the palmitoylated cysteine residue did not seem to be important, as the GAP43(10)-Fyn construct was affected to the same extent as wt Fyn and Gαo(10)-Fyn.

EXAMPLE 14
2-bromopalmitate Inhibits Fatty Acylation and Localization of Palmitoylated Proteins to DRMs in T Cells The Src family kinases Fyn and Lck play critical roles in T cell receptor (TCR) mediated signaling. Palmitoylation of Fyn and Lck has been shown to be essential for localization to detergent resistant microdomains in T cells, and localization to detergent resistant microdomains is required for efficient signaling by the activated TCR (11). The ability of 2-bromopalmitate to inhibit Fyn fatty acylation was tested in Jurkat T cells. Cells were transfected by electroporation with cDNA encoding Fyn. Two days after transfection, cells were labeled with IC13 or IC16 as described above for COS cells. Total protein levels were monitored by immunoprecipitation followed by immunoblotting with anti-Fyn antibody.

Figure 4A:
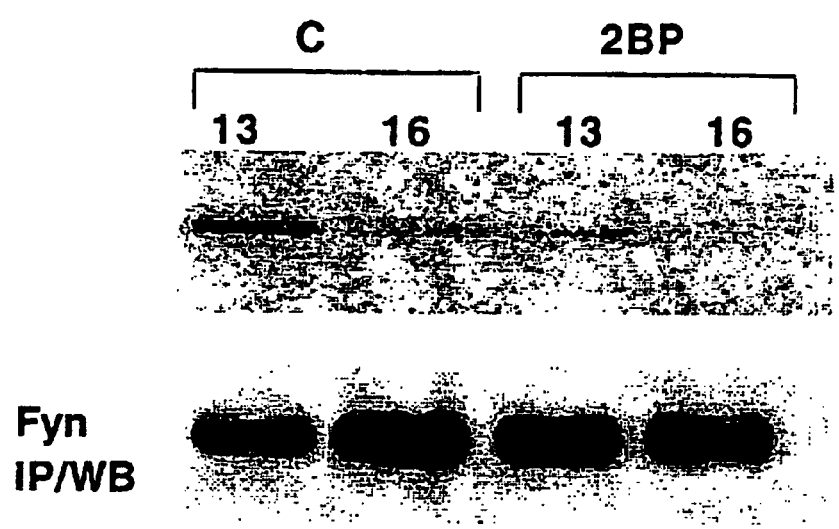
FIG. 4A: cells were radiolabeled for 4 hours in the absence (C) or presence (2BP) of 2-bromopalmitate with $^{125}$I-IC13 or $^{125}$I-IC16 (top panel). Lysates were immunoprecipitated with anti-Fyn antibody. Bottom panel: to monitor total protein levels, aliquots from each sample were subjected to immunoblotting with anti-Fyn antibody.

As depicted in FIG. 4A, myristoylation and palmitoylation were inhibited by 75% and 90% respectively in 2-bromopalmitate treated cells, relative to untreated controls, demonstrating the ability of the reagent to inhibit Fyn fatty acylation in Jurkat T-cells.

Figure 4B:
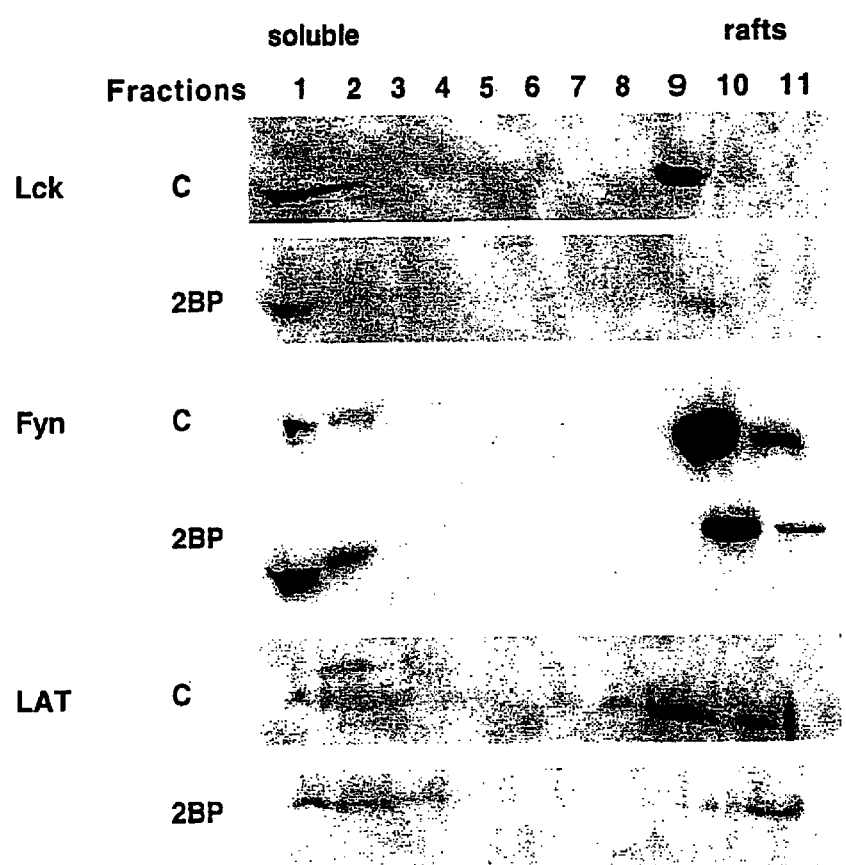
FIG. 4B: Localization to detergent resistant microdomains. Cells were cultured with 2-bromopalmitate as in (FIG. 4A), lysed with buffer containing 0.5% Triton X-100, and layered on the bottom of a sucrose gradient as detailed below. After overnight centrifugation, 1 ml fractions were collected and the DRM localization of endogenous palmitoylated proteins was analyzed by SDS-PAGE and immunoblotting with anti-Lck (top), anti-Fyn (middle) or anti-LAT (bottom) antibodies.

The ability of 2-bromopalmitate to inhibit localization of palmitoylated proteins to detergent resistant microdomains in activated Jurkat cells was examined next. Cells were either left untreated or treated with 100 μM 2-bromopalmitate for 3 hours, washed, resuspended in serum-free media, and the TCR was activated with OKT3 mAb. Activated cells were extracted with Triton X-100 containing buffer. Lysates were layered on the bottom of a sucrose gradient as described above, and subjected to overnight ultracentrifugation. Rafts, which contain detergent resistant microdomains, were collected at the 35%/5% sucrose interface (FIG. 4B, fractions 8–11), whereas fractions 1–4 represented the Triton soluble fractions (FIG. 4B). Each fraction was analyzed by immunoblotting with specific antibodies. 59% of Lck was found in the rafts in control cells, compared with 19% in cells treated with 2-bromopalmitate (Top). Likewise, the amount of Fyn found in the rafts was 88% in control cells, but only 59% in treated cells (middle).

The effect of 2-bromopalmitate on localization of LAT, another palmitoylated protein in T cells that has been shown to be localized to plasma membrane rafts (10,20) was also examined. The majority of LAT (71%) was found in the detergent resistant microdomains in control cells, whereas in cells treated with 2-bromopalmitate only 41% of the protein remained associated with this fraction (bottom). These data indicate that in Jurkat T-cells, 2-bromopalmitate is able to partially block association of endogenous Fyn, Lck and LAT with rafts.

EXAMPLE 15
Effect of 2-bromopalmitate on Tyrosine Phosphorylation in T Cells.

One of the earliest signaling events after T cell receptor activation is the tyrosine phosphorylation of multiple intracellular proteins. The initial phosphorylation events are mediated by activation of Src family kinases. Whether 2-bromopalmitate can interfere with signaling through the T cell receptor was examined by analyzing the ability of the compound to block tyrosine phosphorylation in activated T cells.

Figure 5A:
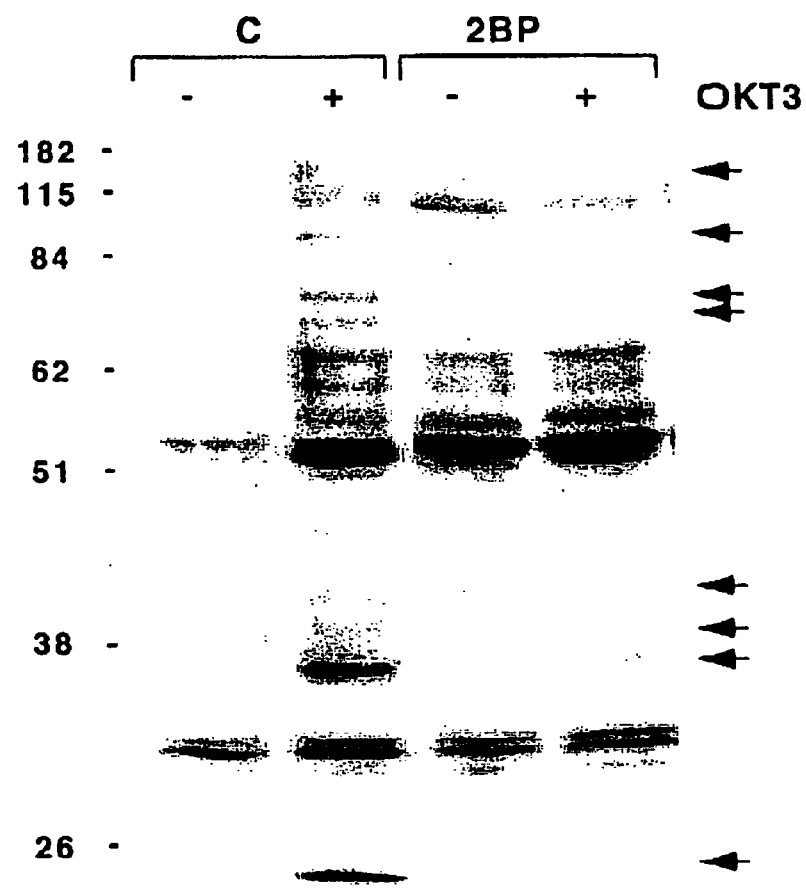
FIG. 5A: Jurkat Cells were treated without or with 2-bromopalmitate for 3 hours, then either were left unactivated (−) or activated (+) with OKT3 mAb (0.3 mg/ml) for 3 minutes and lysed. Lysates were subjected to SDS-PAGE followed by immunoblotting with anti phosphotyrosine antibody (PY99).

Jurkat cells were incubated with 2-bromopalmitate and activated with OKT3 anti-CD3 antibody. Cell lysates were analyzed by immunoblotting with anti phosphotyrosine antibodies. In control cells, stimulation with OKT3 antibodies induced tyrosine phosphorylation of multiple proteins (Fig 5A). In cells treated with 2-bromopalmitate, the phosphorylation of several proteins was significantly inhibited. The most dramatic effect was on a 36 kDa protein, which represents LAT (see below).

In order to identify the individual proteins whose tyrosine phosphorylation is affected by 2-bromopalmitate, lysates were immunoprecipitated with a panel of specific antibodies, and immunoblotted for phosphotyrosine. Alternatively, lysates were immunoprecipitated with an antiphosphotyrosine antibody, and blotted with antibodies to specific proteins.

Figure 5B:
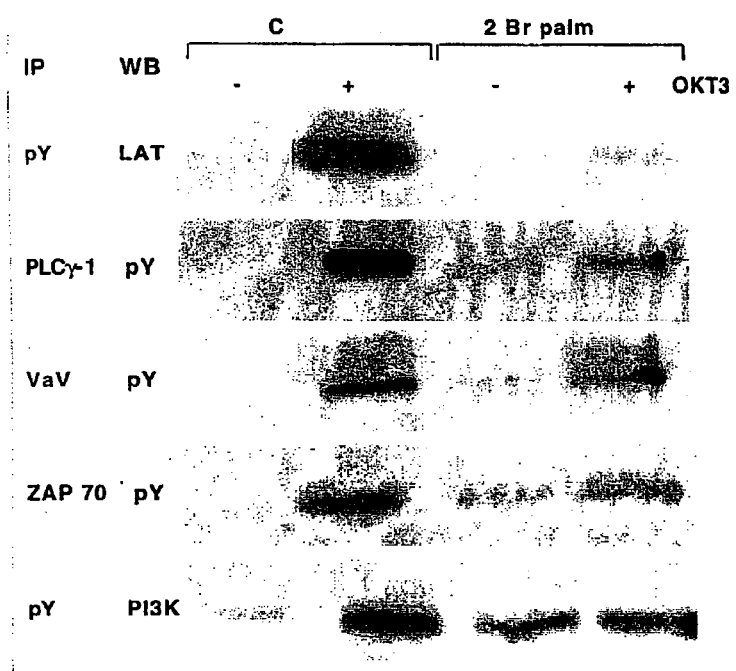
FIG. 5B: cells were treated and lysed as described in (FIG. 5A). Lysates were immunoprecipitated with agarose-conjugated phophotyrosine antibody (PY99) and immunoblotted for specific proteins. Alternatively, lysates were immunoprecipitated for specific proteins and immunoblotted with antiphosphotyrosine antibody, as depicted in the figure.

FIG. 5B shows that in 2-bromopalmitate treated cells, CD3-mediated tyrosine phosphorylation of LAT was inhibited completely. PLC-γ1 phosphorylation was inhibited by 70%, Vav phosphorylation was inhibited by 40%, ZAP-70 phosphorylation was inhibited by 50%, and PI3K phosphorylation was inhibited by 50%. Low to moderate increases in tyrosine phosphorylation were observed in the presence of 2-bromopalmitate alone for some of the proteins. The reason for this basal activation is unknown.

To verify that the observed inhibition of T cell receptor-mediated tyrosine phosphorylation was not a result of toxicity effects of 2-bromopalmitate, aliquots of each sample were analyzed by immunoblotting with anti-LAT and anti-actin antibodies. The levels of LAT and actin were not affected by 2-bromopalmitate (data not shown). Thus 2-bromopalmitate was able to inhibit signaling through the T cell receptor, as assayed by its ability to inhibit tyrosine phosphorylation of key substrate proteins.

EXAMPLE 16
2-bromopalmitate Inhibits Calcium Mobilization in T Cells

T cell receptor activation results in increased $Ca^{++}$ mobilization in stimulated T cells. The increase in $Ca^{++}$ flux is mediated by tyrosine phosphorylation and activation of PLC-γl. PLC-γl hydrolyzes phosphatidylinositol 4,5-bisphosphate (PIP2) to inositol 1,4,5-triphosphate (IP3), which promotes calcium release from the ER (46). The ability of 2-bromopalmitate to interfere with calcium release was assayed next by flow cytometry.

Figures 1, 6A:
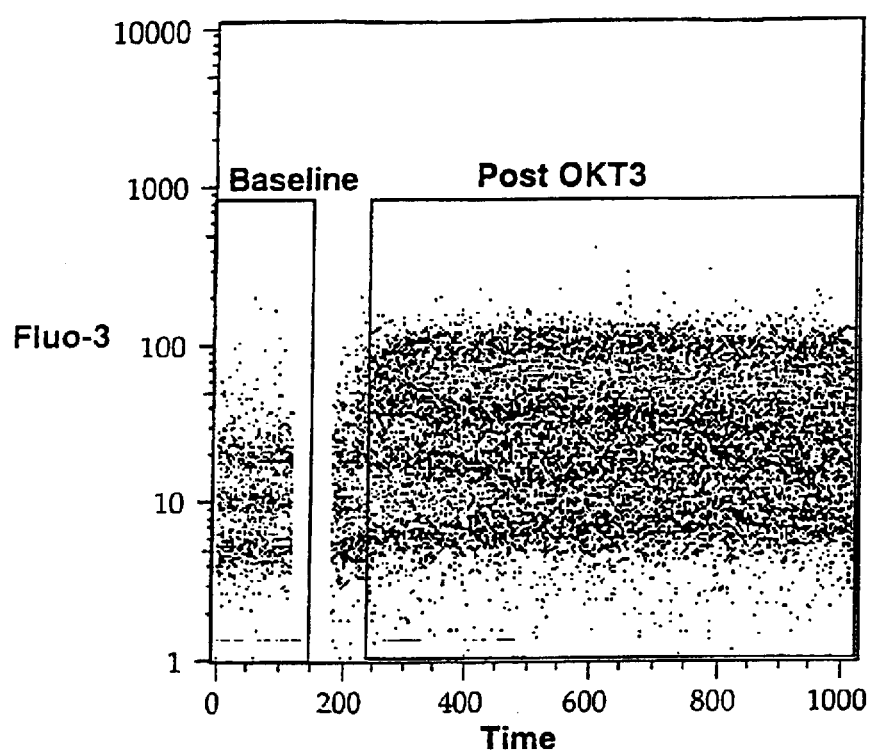
Figures 2, 6A:
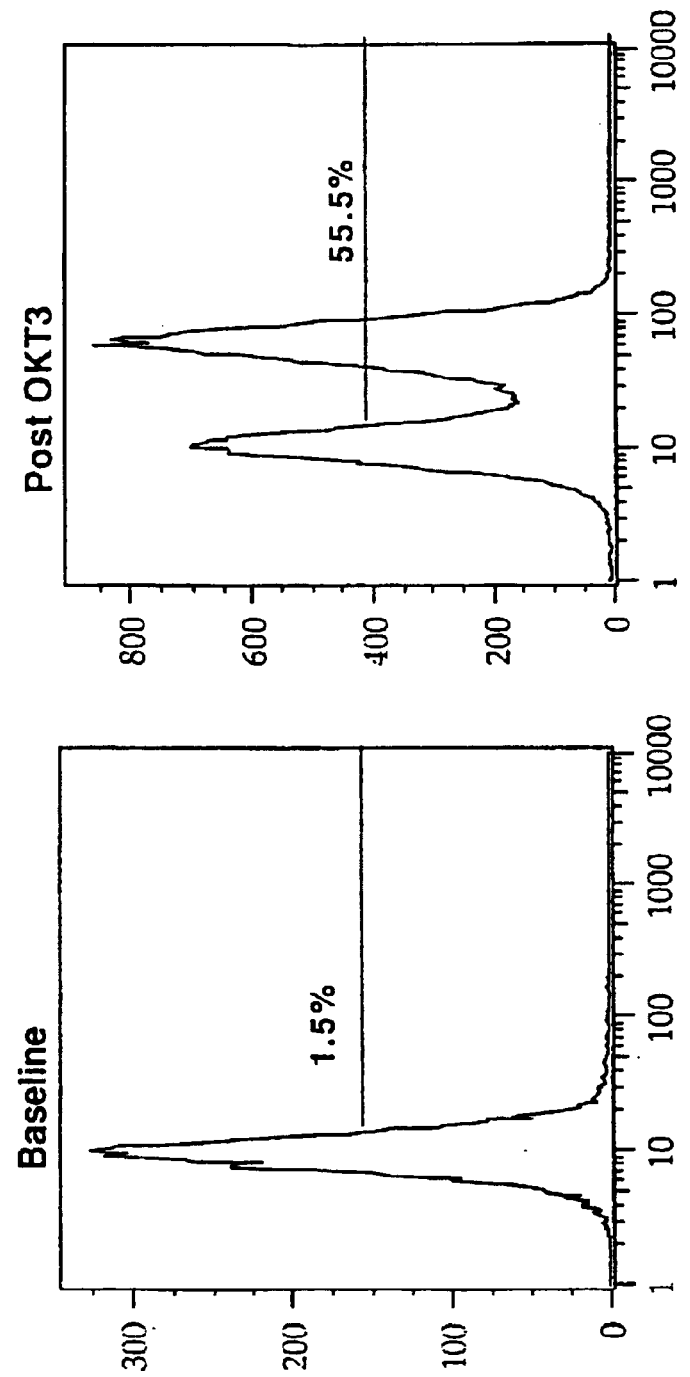
Figures 1, 6B:
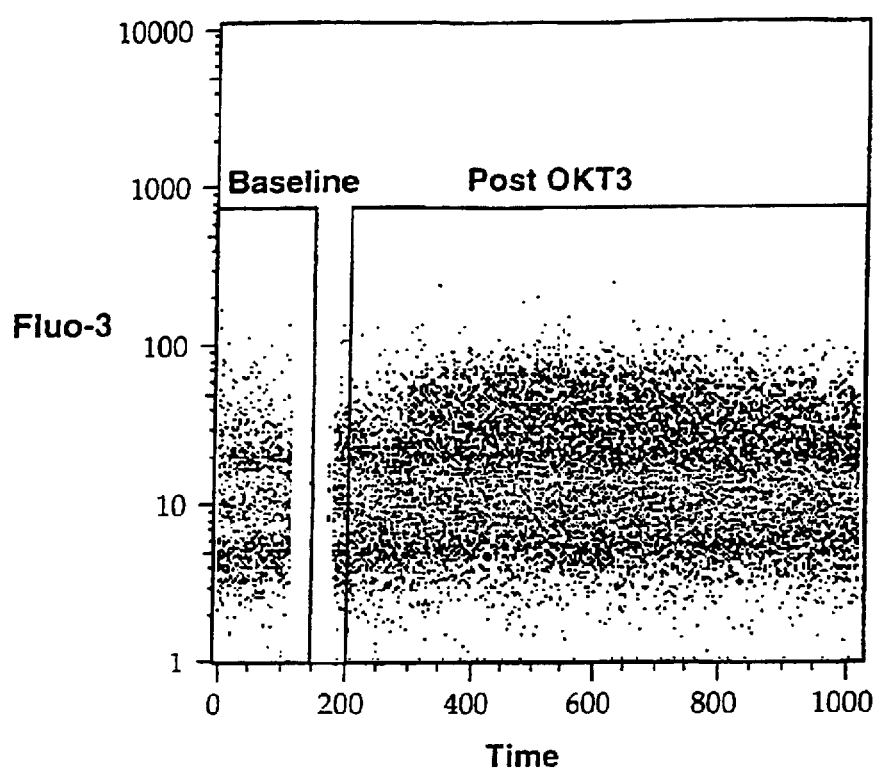
Figures 2, 6B:
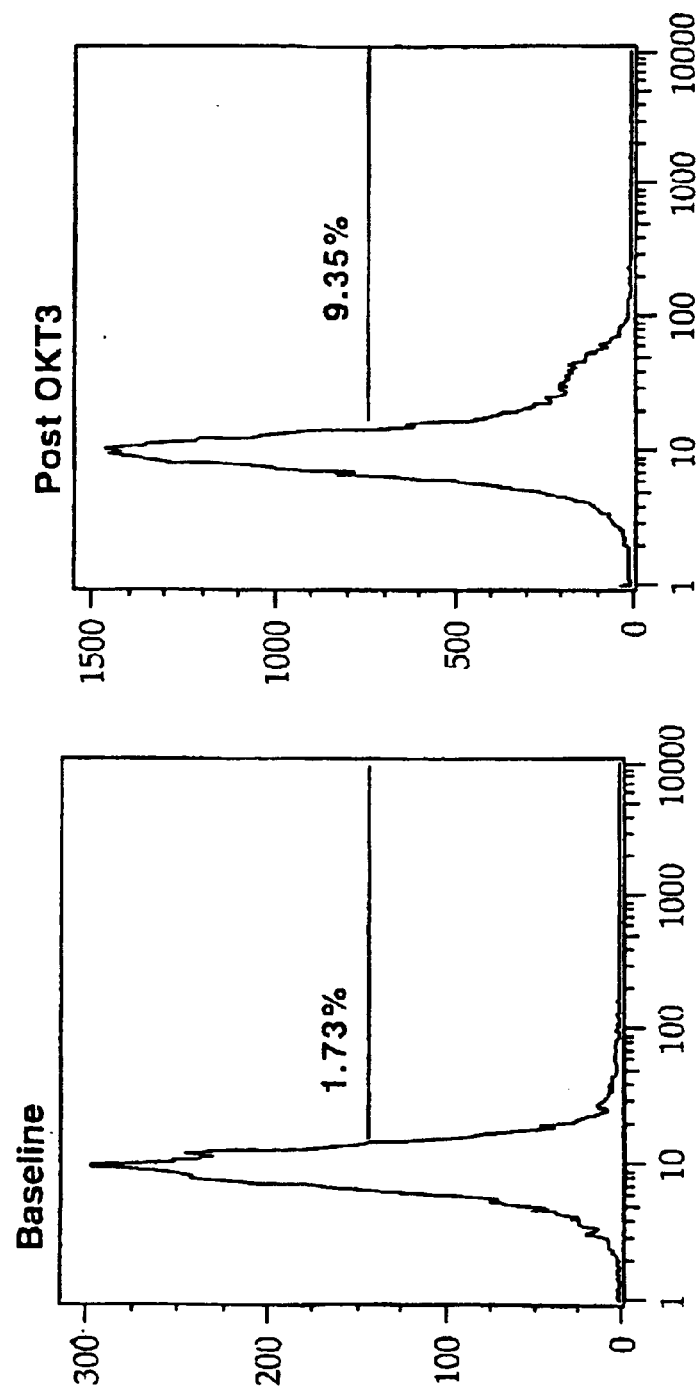

Jurkat cells were incubated with or without 2-bromopalmitate, washed and stained with the fluorescent dye fluo-3 (50 µM). Cells were activated with OKT3 antibody and analyzed by flow cytometry. FIG. 5 shows that in response to T cell receptor activation, T cells treated with 2-bromopalmitate were severely impaired in their ability to release calcium compared with control cells (FIGS. 6A and 6B). Quantitation of the data revealed that calcium flux shut down almost completely in the presence of 2-bromopalmitate. No effect of 2-bromopalmitate on cells incubated in the absence of OKT3 was noted.

To ensure that the observed inhibition of calcium flux was not due to a decreased expression of CD3 in 2bromo-palmitate treated cells, Jurkat cells were incubated with OKT3 antibody at 0° C., followed by incubation with a Fluorescein (FITC) conjugated Goat Anti-Mouse secondary antibody. The percentage of CD3 positive cells was analyzed by FACS analysis. Over 95% of the cells were found to be positive for CD3 in control and 2-bromopalmitate treated cells (data not shown).

EXAMPLE 17
2-bromopalmitate Inhibits MAP Kinase Activation

Figure 7:
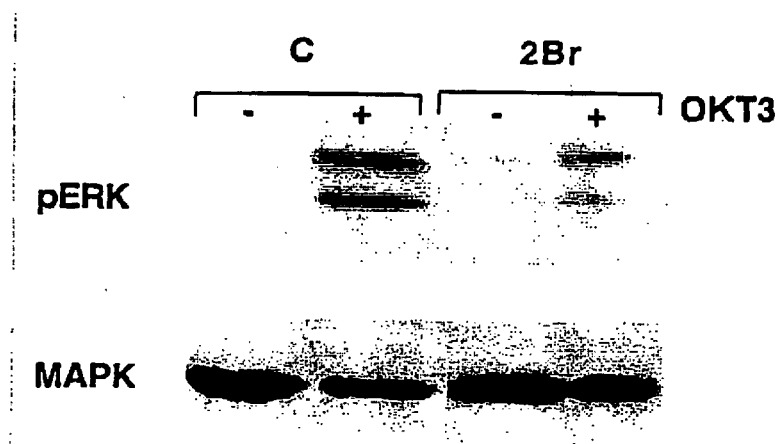
FIG. 7 shows the activation of MAP Kinase in Jurkat Cells. Cells were treated with 2-bromopalmitate, activated with OKT3 mAb and lysed. Lysates were subjected to SDS-PAGE and immublotted for active (Top—pERK), or for total (bottom—MAPK) MAP Kinase.

One of the proximal events following T cell receptor engagement is activation of the MAP Kinase pathway. The ability of 2-bromopalmitate to inhibit activation of MAP kinase was examined in Jurkat cells. Cells were cultured with or without 2bromo-palmitate and activated as described above. Cell lysates were subjected to SDS-PAGE and immunoblotted with anti-active MAPK kinase (pERK1). As depicted in FIG. 7, 2-bromopalmitate inhibited the activation of MAPK kinase by 70%. The levels of total MAPK kinase remained unchanged (FIG. 7).

EXAMPLE 18
PUFAs Inhibit Fyn Palmitoylation and Localization to DRMs in COS-1 Cells The data reported above identify 2-bromopalmitate as an inhibitor of protein fatty acylation and T cell receptor-mediated signaling. Whether other fatty acids, particularly long chain unsaturated compounds, might also interfere with protein fatty acylation was examined next. It has recently been reported that polyunsaturated fatty acids inhibit T cell signal transduction by displacing Src kinases Fyn and Lck from the detergent resistant microdomains (37). This inhibition was speculated to be due to polyunsaturated fatty acid-induced disruption of DRM structure and composition. Based on these results with 2-bromopalmitate, polyunsaturated fatty acid-induced displacement of Fyn/Lck from the detergent resistant microdomains may actually be due to alterations of S-acylation.

To test this hypothesis, Fyn transfected COS-1 cells were incubated O/N with or without 50 µM arachidonic acid (20:4) or eicosapentaenoic acid (20:5), then labeled with IC13 or IC16. Total protein levels were monitored by immunoblotting aliquots of each sample with anti-Fyn antibody (FIG. 8A, lower panel).

Figure 8A:
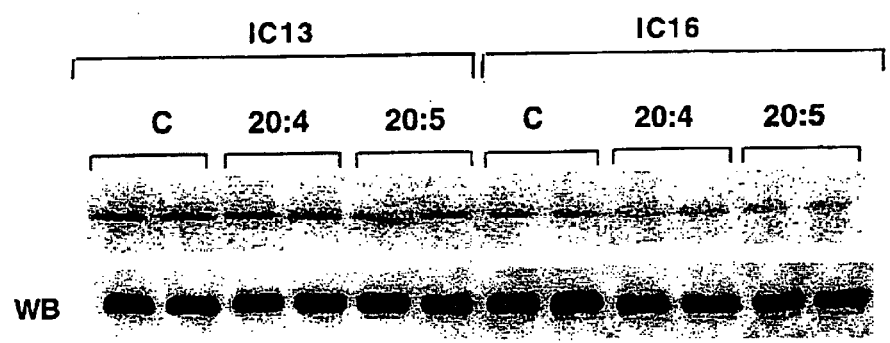
FIG. 8A shows the cells were radiolabeled for 4 hours in the absence (C) or presence of 20:4 or 20:5 with $I^{125}IC13$ or $I^{125}$-IC16, lysed and duplicate samples were subjected to immunoprecipitation with anti-Fyn antibody. Lysates were subjected to SDS-PAGE and phosphorimaging (top). Bottom: to monitor total protein levels, aliquots from each sample were subjected to SDS-PAGE followed by immunoblotting with anti-Fyn antibody.
Figure 8B:
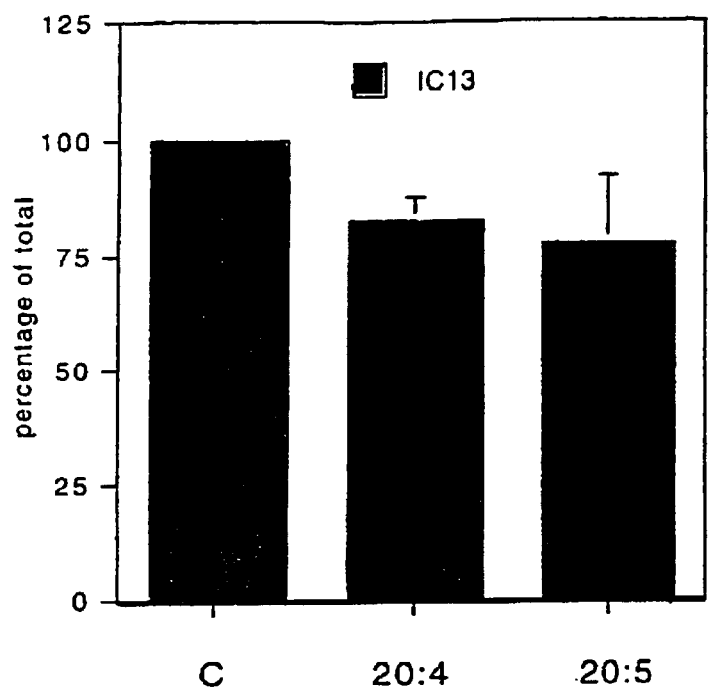
FIG. 8B and FIG. 8C: Quantitation of (FIG. 5A). Effect of polyunsaturated fatty acids on IC13 (FIG. 8B) or IC16 (FIG. 8C) incorporation into Fyn. Bars represent the average of 3 sets of duplicate experiments.
Figure 8C:
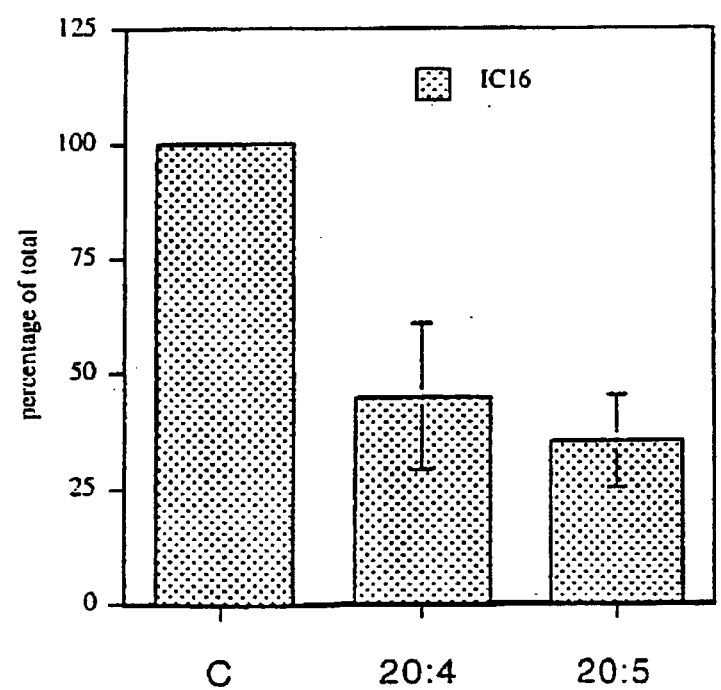

As depicted in FIG. 8A, Fyn myristoylation was not affected by polyunsaturated fatty acid treatment to a significant effect (FIG. 8B). On the other hand, Fyn palmitoylation was affected quite dramatically. Arachidonic acid inhibited incorporation of IC16 into Fyn by 55%, and eicosapentaenoic acid by 65% (FIG. 8C). These reductions in palmitate incorporation correlate well with the previously reported observation that 20:5 is slightly more potent than 20:4 in inhibiting T cell signaling and in displacing Fyn and Lck from detergent resistant microdomains (37). In the same report, the polyunsaturated fatty acid docosahexaenoic acid (22:6) was less active than 20:4 and 20:5, and only moderately inhibited Fyn/Lck displacement from detergent resistant microdomains and TCR signaling. In agreement with these findings, 22:6 was 10–20% less potent than 20:4 and 20:5 at inhibiting Fyn palmitoylation (data not shown).

Whether 20:4 and 20:5 inhibited localization of Fyn to detergent resistant microdomains in COS-1 cells was examined next. Cells were treated with or without polyunsaturated fatty acids as described above and layered on the bottom of a sucrose gradient as described above. Fractions were collected and analyzed by immunoblotting with anti-Fyn antibody.

Figure 8D:
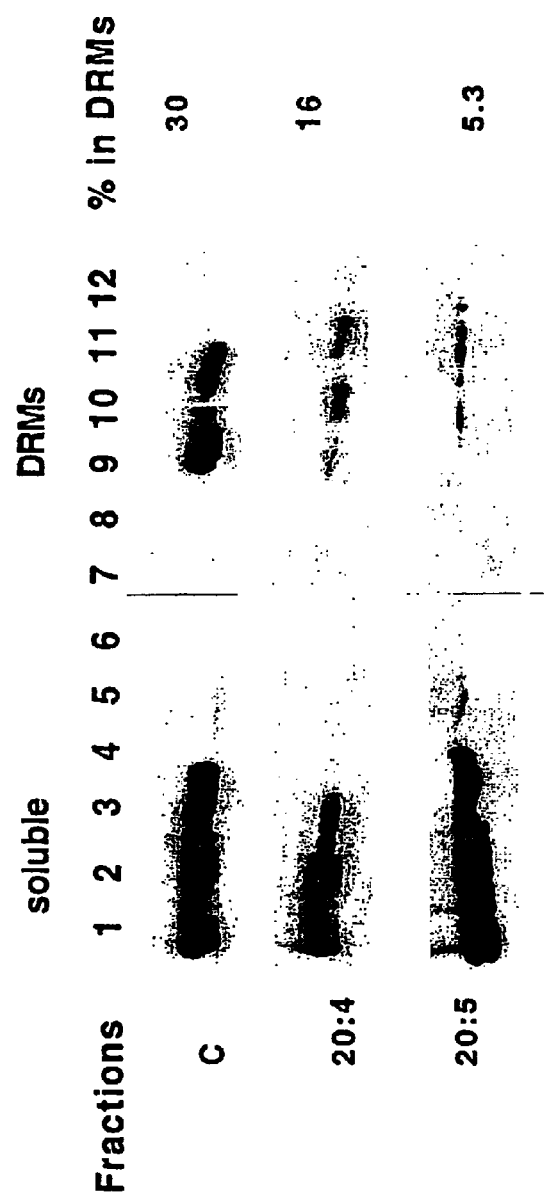
FIG. 8D: DRM localization. Cells were lysed with buffer containing 0.5% Triton X-100, and layered on the bottom of a sucrose gradient as detailed below. After overnight centrifugations, 1 ml fractions were collected and the DRM localization of Fyn was analyzed by SDS-PAGE and immunoblotting with anti-Fyn antibody.

As depicted in FIG. 8D, in untreated cells, 30% of Fyn localized to detergent resistant microdomains, in agreement with previous findings (47). Treatment with polyunsaturated fatty acids markedly reduced the ability of Fyn to localize to detergent resistant microdomains, with only 16% of Fyn found in detergent resistant microdomains in 20:4 treated cells, and 5.3% in 20:5 treated cells. These finding clearly demonstrate that the displacement of Fyn from detergent resistant microdomains is likely due to a polyunsaturated fatty acid-induced reduction in Fyn palmitoylation.

Discussion
2-bromopalmitate inhibits Fyn fatty acylation in COS-1 cells

The ability of Src family members Fyn and Lck to participate in signaling through the T-cell receptor is critically dependent on their fatty acylation with myristate and palmitate. In this study, 2-bromopalmitate was identified as an inhibitor of Fyn fatty acylation and membrane targeting. This was accomplished by screening palmitate analogs for their ability to inhibit incorporation of myristate and palmitate into Fyn in transiently transfected COS-1 cells. This inhibition results in decreased membrane binding and localization to detergent resistant microdomains. Moreover, 2-bromopalmitate inhibits fatty acylation and localization of Fyn, Lck and LAT to detergent resistant microdomains in Jurkat T cells. Consequently, this results in impaired signaling through the T-cell receptor, as shown by a reduction in tyrosine phosphorylation, calcium flux and activation of the MAP kinase pathway. Furthermore, polyunsaturated fatty acids arachidonic acid (20:4) and eicosapentaenoic acid (20:5) are specific inhibitors of Fyn palmitoylation and localization to detergent resistant microdomains in COS-1 cells. This may account for the ability of these compounds to inhibit T cell signaling as reported previously (37), and may be a mechanism by which these agents exert their immunosuppressive and anti-inflammatory effects.

Protein palmitoylation occurs within an N-terminal myr-gly-cys motif, and that this event is dependent on myristoylation (12,13). The ability of 2-bromopalmitate to partially inhibit myristoylation likely accounts for some of the reduction in palmitoylation. However, the extent of inhibition by 2-bromopalmitate on Fyn palmitoylation is always greater than that on myristoylation, implying that 2-bromopalmitate has additional, direct effects on palmitoylation (FIGS. 1A, 4A). A direct effect on palmitoylation is also supported by the observation that 2-bromopalmitate inhibits membrane localization of a GAP43(10)-Fyn construct, which is palmitoylated but not myristoylated (FIG. 3B). Furthermore, 2-hydroxymyristate, a known inhibitor of myristoylation (40,41), inhibits membrane localization of Fyn and Fyn(16)-eGFP to a greater extent than 2-bromopalmitate (FIG. 2B). This implies that 2-bromopalmitate treated cells contain a population of myristoylated, non-palmitoylated Fyn that has a greater affinity for membranes than non-acylated Fyn. Finally, the membrane localization of Fyn in the presence of 2-bromopalmitate resembles that of the myristoylated, non-palmitoylated C3,6S Fyn mutant previously studied (13). Thus, 2-bromopalmitate is an inhibitor of protein fatty acylation with some specificity for palmitoylation.

Two possible mechanisms may account for the inhibitory effect of 2-bromopalmitate on palmitoylation. One possibility is that 2-bromopalmitate binds to PAT, but because of the steric bulk of the bromine, it cannot be transferred to the acceptor protein. Alternatively, 2-bromopalmitate may serve as a substrate for PAT. In this case, Fyn would be S-acylated with 2-bromopalmitate, but hydrophilic and steric effects of the bromine atom would reduce the protein's affinity for membranes. In the absence of a radiolabeled form of 2-bromopalmitate, it is not possible at this point to distinguish between these two possibilities.

2-bromopalmitate Inhibits Fyn Fatty Acylation and Signaling in Jurkat T Cells

The experiments depicted in FIG. 4 indicate that 2-bromopalmitate inhibits Fyn fatty acylation and localization to detergent resistant microdomains in Jurkat T cells. As a result, there is a marked reduction in tyrosine phosphorylation of key signaling molecules in CD3 stimulated cells (FIG. 5), suggesting that signaling via the TCR is impaired. Interestingly, some proteins show an increase in the level of phosphorylation in 2-bromopalmitate treated cells as compared to control cells, even in the absence of CD3 stimulation. While the basis for this basal activation is unknown, it does not seem to be related to TCR activation, since there is no effect on $Ca^{+2}$ flux or activation of MAP kinase pathway in unstimulated 2-bromopalmitate treated cells. If this basal activation is taken into account, then the reduction of tyrosine phosphorylation on the signaling molecules examined ranges from 70–100% (FIG. 5B).

PUFAs inhibit Fyn palmitoylation and localization to DRMs in COS-1 cells

Polyunsaturated fatty acids modulate immune responses by affecting T cell function (48). Therefore these agents (particularly the n-3 series) have found clinical applications in the treatment of various inflammatory diseases such as rheumatoid arthritis and Crohn's disease relapses (33,35,36) and as immunosuppressive agents (32). Despite the broad clinical use of polyunsaturated fatty acids, the mechanism of polyunsaturated fatty acid-induced T cell inhibition had not been elucidated. Recently, it was reported that the polyunsaturated fatty acid-induced inhibition of T cell activation is due to displacement of Src family kinases from the cytoplasmic layer of the detergent resistant microdomains (37). This displacement was hypothesized to be mediated by modification of the DRM structure and composition. Here it was shown that the exclusion of Src family kinase Fyn from detergent resistant microdomains in polyunsaturated fatty acid-treated cells is due to inhibition of palmitoylation.

In contrast to the saturated inhibitor 2-bromopalmitate, polyunsaturated arachidonic acid (20:4) and eicosapentaenoic acid (20:5) have almost no effect on Fyn myristoylation, and are rather specific for palmitoylation. Several lines of evidence suggest that the mechanism of inhibition of palmitoylation involves the use of polyunsaturated fatty acids as alternative substrates for S-acylation to Fyn. First, studies of partially purified preparations of PAT reveal that longer chain fatty acyl CoAs, including stearate (18:0) and arachidonate (20:4) can compete with palmitate for incorporation into Fyn and Gαo (26,27). Secondly, Gα subunits, P-selectin, asialoglycoprotein receptor and several platelet proteins have been shown to be S-acylated with stearate, arachidonate and eicosapentaenoate, in addition to palmitate (49,50). These results indicate that the fatty acid specificity of PAT and S-acylation is loose in vivo and in vitro. Thirdly, Fyn localization to the plasma membrane fraction is not affected by polyunsaturated fatty acids (data not shown), even though incorporation of $^{125}$I-IC16 is markedly reduced. Since myristoylation alone is not sufficient for stable membrane binding, it is likely that Fyn becomes dually fatty acylated by N-myristoylation and S-acylation with a polyunsaturated fatty acid. The presence of myristate and polyunsaturated fatty acid at the N-terminus of Fyn would provide strong affinity for binding to a membrane bilayer. However, the presence of a polyunsaturated, bulky acyl chain in the polyunsaturated fatty acid would preclude specific localization to DRMS which, due to their liquid ordered domain structure, provide a local environment conducive to insertion of saturated, but not unsaturated fatty acid chains (18).

In conclusion, specific fatty acids and fatty acid analogs function as inhibitors of protein fatty acylation and TCR mediated signaling. The advantage of using inhibitors that interfere with subcellular localization of a key protein is that it allows one to study signaling by endogenous cellular proteins and eliminates the need to overexpress mutant proteins. Thus, 2-bromopalmitate can be used as a powerful tool to study the role of Src kinases in the endogenous T cell signaling system, and may provide insight into the role of signaling in the onset of disease. PUFA-induced inhibition of T cells is likely due to the inhibition of Src kinase palmitoylation. Though these agents are currently used in the clinic, their mechanism of action is still largely unknown. A novel mechanism, inhibition of protein palmitoylation, may account for the abilities of polyunsaturated fatty acids to treat or prevent a broad range of immune-based diseases.

The following references were cited herein:
1. Resh, M. D. (1994) Cell 76, 422–413
2. Resh, M. D. (1996) Cell Signaling 8, 403–412
3. Johnson, et al., (1994) Annu. Rev. Biochem. 63, 869–914
4. Towler, D. and Gordon, J. (1988) Ann. Rev. Biochem. 57, 69–99
5. Gordon, et al., (1991) J. Biol. Chem. 266, 8647–8650
6. Cross, et al., (1984) Mot. Cell Biol. 4, 1834–1842
7. Kamps, et al., (1985) Proc. Natl. Acad. Sci. U.S.A. 87, 4625–4628
8. Peitzsch, et al., (1993) Biochemistry 32, 10436–10443
9. Alland, et al., (1994) J. Biol. Chem 269(24), 16701–16705
10. Zhang, et al., (1998) Cell 92, 83–92
11. Kabouridis, et al., (1997) EMBO Journal 16, 4983–4998
12. van't Hof, W., and Resh, M. (1997) J. Cell Biol. 136, 1023–1035
13. Wolven, et al., (1997) Mol. Biol. Cell, in press
14. Shenoyscaria, et al., (1994) J. Cell Biol. 126, 353–363
15. Shaul, et al., (1996) J. Biol. Chem. 271, 6518–6522
16. Rodgers, et al., (1994) Mol. Cell. Biol. 14, 5384–5391
17. Schnitzer, et al., (1995) Science 269, 1435–1439

18. Brown, et al., (1997) *Biochem. & Biophys. Res. Commun.* 240, 1–7
19. Xavier, et al., (1998) *Immunity* 8, 723–32
20. Zhang, W., Trible, R. P., (1998) *Immunity* 9, 239–246
21. Montixi, et al., (1998) *EMBO J.* 17, 5334–5348
22. Mustelin, et al., (1993) *Trends Biochem. Sci.* 18, 215–220
23. van't Hof, W., and Resh, M. D. (1999) *J. Cell Biol.* 145, 377–389
24. Camp, et al., (1994) *J. Biol. Chem.* 269, 23212–23219
25. Duncan, et al., (1998) *J. Biol. Chem.* 272, 27456–27463
26. Berthiaume, et al., (1995) *J. Biol. Chem.* 270, 22399–22405
27. Dunphy, et al., (1996) *J. Biol. Chem.* 271, 7154–7159
28. Das, et al., (1997) *J. Biol. Chem.* 272, 11021–11025
29. Duncan, et al., (1996) *J. Biol. Chem.* 271, 23594–23600
30. Bano, et al., (1998) *Biochem. J.* 330, 723–731
31. Hepler, et al., (1996) *J. Biol. Chem.* 271, 496–504
32. Van der Heide, et al., (1993) *N. Engl. J. Med.* 329, 769–773
33. Belluzzi, et al., (1996) *N. Engl. J. Med.* 334, 1557–1560
34. Cappelli, et al., (1997) *J. Nephrol.* 10, 157–162
35. Cleland, et al., (1988) *J. Rheumatol.* 15, 1171–1475
36. Kremer, et al., (1987) *Ann. Int. Med.* 106, 497–504
37. Stulnig, et al., (1998) *J. Cell Biol.* 143, 637–644
38. Towers, et al., (1999) *Mol. Cell. Biol.* 19, 4191–4199
39. Peseckis, et al., (1993) *J. Biol. Chem.* 268, 5107–5114
40. Paige, et al., (1989) *J. Med. Chem.* 32, 1665–1667
41. Paige, et al., (1990) *Biochemistry* 29, 10566–10573
42. Linder, et al., (1993) *Proc. Natl. Acad. Sci. USA* 90, 3675–3679
43. Parenti, et al., (1993) *Biochem. J.* 291, 349–353
44. Liu, et al., (1993) *Biochemistry* 32, 10714–10719
45. Hancock, et al., (1989) *Cell* 57, 1167–1177
46. Rhee, S., and Bae, Y. (1997) *J. Biol. Chem.* 272, 15045–15048
47. Ilangumaran, et al., (1999) *Mol. Biol. Cell* 10, 891–905
48. Zurier, R. (1.993) *Prostaglandin's Leukot. Essent. Fatty Acids* 48,
49. Van Cott, et al., (1997) *Prostaglandins Leukot. Essent. Fatty Acids* 57, 33–37
50. Hallak, et al., (1994) *J. Biol. Chem.* 269, 4713–4716

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inhibiting Fyn/Lck fatty acylation and protein palmitoylation in a cell In an individual having autoimmune disease comprising:

administering to said individual a pharmacologically effective dose of 2-bromopalmitate.

2. The method of claim 1, wherein said 2-bromopalmitate is administered in a dose of about 0.1 mg/kg to about 100 mg/kg of total body weight of said individual.

3. The method of claim 1, wherein said 2-bromopalmitate inhibits protein palmitoylation within the N-terminus of the proteins.

4. The method of claim 1, wherein said 2-bromopalmitate further inhibits myristoylation of proteins.

5. The method of claim 1, wherein inhibiting Fyn/Lck fatty acylation further inhibits T cell signaling events.

6. The method of claim 1, wherein said autoimmune disease is rheumatoid arthritis, Crohn's disease, diabetes, multiple sclerosis or systemic lupus erythematosus.

7. A method of inhibiting T-cell receptor mediated signaling events in an individual having an autoimmune disease comprising:

administering to said individual a pharmacologically effective dose of 2-bromopalmitate; wherein 2-bromopalmitate inhibits Fyn/Lck fatty acylation in the T-cells thereby inhibiting T-cell receptor mediated signaling events in the individual.

8. The method of claim 7, wherein said 2-bromopalmitate is administered in a dose of about 0.1 to about 100 mg/kg of total body weight of said individual.

9. The method of claim 7, wherein said autoimmune disease is rheumatoid arthritis, diabetes, Crohn's disease, multiple sclerosis or systemic lupus erythematosus.

* * * * *